United States Patent
Iwabuchi et al.

(10) Patent No.: US 7,232,996 B2
(45) Date of Patent: *Jun. 19, 2007

(54) METHOD AND AN APPARATUS OF AN INSPECTION SYSTEM USING AN ELECTRON BEAM

(75) Inventors: Yuko Iwabuchi, Mito (JP); Hideo Todokoro, Nishitama-gun (JP); Hiroyoshi Mori, Hitachinaka (JP); Mitsugu Sato, Hitachinaka (JP); Yasutsugu Usami, Toshina-ku (JP); Mikio Ichihashi, Kodaria (JP); Satoru Fukuhara, Hitachinaka (JP); Hiroyuki Shinada, Chofu (JP); Yutaka Kaneko, Hachiouji (JP); Katsuya Sugiyama, Kashiwa (JP); Atsuko Takafuji, Nerima-ku (JP); Hiroshi Toyama, Hachiouji (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/319,279

(22) Filed: Dec. 29, 2005

(65) Prior Publication Data

US 2006/0151699 A1 Jul. 13, 2006

Related U.S. Application Data

(63) Continuation of application No. 11/108,877, filed on Apr. 19, 2005, now Pat. No. 7,012,252, which is a continuation of application No. 10/083,481, filed on Feb. 27, 2002, now Pat. No. 6,987,265, which is a continuation of application No. 09/883,184, filed on Jun. 19, 2001, now Pat. No. 6,452,178, which is a continuation of application No. 09/131,383, filed on Aug. 7, 1998, now Pat. No. 6,348,690.

(30) Foreign Application Priority Data

Aug. 7, 1997 (JP) ................... 9-212908

(51) Int. Cl.
*H01J 37/28* (2006.01)
(52) U.S. Cl. ...................................... 250/310; 250/307
(58) Field of Classification Search .................... None
See application file for complete search history.

(56) References Cited

U.S. PATENT DOCUMENTS 3,736,422 A * 5/1973 Weber et al. ............... 250/310

(Continued)

FOREIGN PATENT DOCUMENTS

JP 51-16861 A 2/1976

(Continued)

*Primary Examiner*—Jack I. Berman
(74) *Attorney, Agent, or Firm*—Kenyon & Kenyon LLP

(57) ABSTRACT

Problems encountered in the conventional inspection method and the conventional apparatus adopting the method are solved by the present invention using an electron beam by providing a novel inspection method and an inspection apparatus adopting the novel method which are capable of increasing the speed to scan a specimen such as a semiconductor wafer.

The inspection novel method provided by the present invention comprises the steps of: generating an electron beam; converging the generated electron beam on a specimen by using an objective lens; scanning the specimen by using the converged electron beam; continuously moving the specimen during scanning; detecting charged particles emanating from the specimen at a location between the specimen and the objective lens and converting the detected charged particles into an electrical signal; storing picture information conveyed by the electrical signal; comparing a picture with another by using the stored picture information; and detecting a defect of the specimen.

12 Claims, 10 Drawing Sheets

U.S. PATENT DOCUMENTS

| | | |
|---|---|---|
| 4,713,543 A | 12/1987 | Feuerbaum et al. |
| 4,714,833 A | 12/1987 | Rose et al. |
| 5,146,089 A | 9/1992 | Rosien |
| 5,214,284 A | 5/1993 | Tokunaga et al. |
| 5,276,325 A | 1/1994 | Todokoro et al. |
| 5,401,974 A | 3/1995 | Oae et al. |
| 5,502,306 A | 3/1996 | Meisburger et al. |
| 5,578,821 A | 11/1996 | Meisberger et al. |
| 5,872,358 A | 2/1999 | Todokoro et al. |
| 6,172,363 B1 | 1/2001 | Shinada et al. |
| 6,348,690 B1 | 2/2002 | Iwabuchi et al. |
| 6,452,178 B2 | 9/2002 | Iwabuchi et al. |

FOREIGN PATENT DOCUMENTS

| | | |
|---|---|---|
| JP | A 54-67367 | 5/1979 |
| JP | A 58-4255 | 1/1983 |
| JP | 2-015546 | 1/1990 |
| JP | 2-121252 | 5/1990 |
| JP | 2-189848 | 7/1990 |
| JP | 4-297051 | 10/1992 |
| JP | 4-322048 | 11/1992 |
| JP | 5-074399 | 3/1993 |
| JP | 5-128989 | 5/1993 |
| JP | 5-251525 | 9/1993 |
| JP | A 5-258703 | 10/1993 |
| JP | A 5-343021 | 12/1993 |
| JP | 6-020634 | 1/1994 |
| JP | 6-310074 | 11/1994 |
| JP | 6-325709 | 11/1994 |
| JP | 7-243999 | 9/1995 |
| JP | 7-286842 | 10/1995 |
| JP | 7-306028 | 11/1995 |
| JP | A 8-212955 | 8/1996 |
| JP | 9-082261 | 3/1997 |
| JP | 9-082264 | 3/1997 |

\* cited by examiner

NORMALLY FABRICATED PATTERN

PATTERN HAVING A DEFECT

A : ISOLATED DEFECT
B : PROTRUSION
C : SHORT
D : OMISSION
E : DISCONNECTION
F : THIN FILM RESIDUAL
G : BAD APERTURE

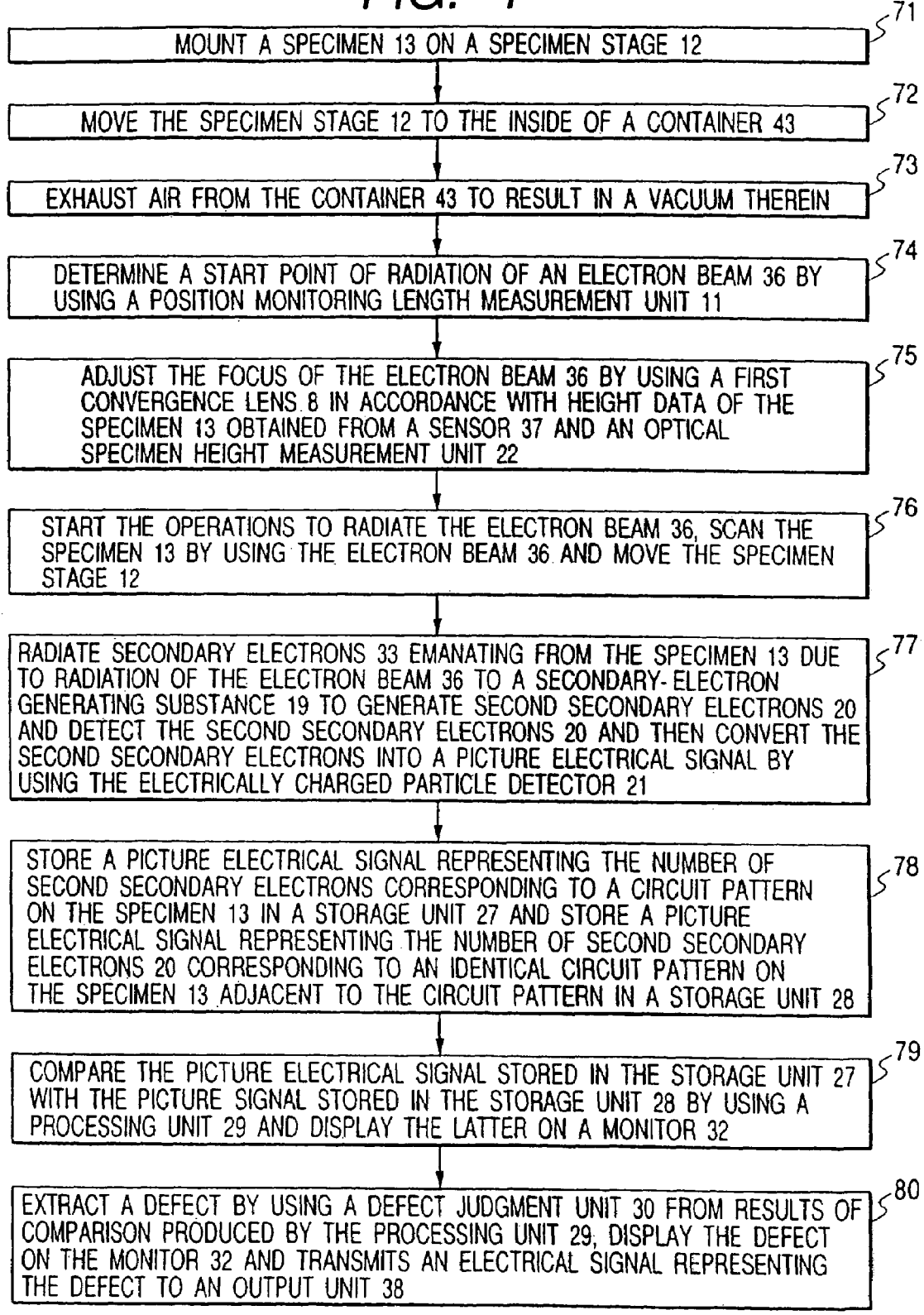

PICTURE 1

PICTURE 2

PICTURE OF DIFFERENCE

DEFECT

US 7,232,996 B2

METHOD AND AN APPARATUS OF AN INSPECTION SYSTEM USING AN ELECTRON BEAM

This is a continuation of application Ser. No. 11/108,877 filed Apr. 19, 2005 now U.S. Pat. No. 7,012,252, which is a continuation of application Ser. No. 10/083,481 filed Feb. 27, 2002 now U.S. Pat. No. 6,987,265, which is a continuation of application Ser. No. 09/883,184, filed Jun. 19, 2001, which issued as U.S. Pat. No. 6,452,178 on Sep. 17, 2002, which is a continuation of application Ser. No. 09/131,383 filed Aug. 7, 1998, which issued as U.S. Pat. 6,348,690 on Feb. 19, 2002.

FIELD OF THE INVENTION

In general, the present invention relates to an inspection method using an electron beam and an inspection apparatus adopting the method. More particularly, the present invention relates to an inspection method using an electron beam suitably for inspecting a pattern such as a circuit on a substrate in a process of fabricating a semiconductor device and an inspection apparatus adopting the method.

BACKGROUND OF THE INVENTION

There exists an apparatus for observing a specimen by using an electron beam which is known as a scanning electron microscope referred to hereafter simply as an SEM. In addition, as one of apparatuses for inspecting a semiconductor device, there is known a scanning electron microscope for length measurement referred to as a length measurement SEM. However, while the ordinary SEM and the length measurement SEM are suited for observation of a limited field of vision at a high magnification, they are unsuitable for finding the location of a defect on a wafer. This is because, in order to find the location of a defect on a wafer, it is necessary to search an extremely large area of the wafer or the entire surface of the wafer with a high degree of scrutiny. It takes a very long time to search such an extremely large area by using an ordinary or length measurement SEM because the current of the electron beam thereof is small, resulting in a slow scanning speed. As a result, if such SEMs are used in a process to fabricate a semiconductor device, the time it takes to complete the processing steps becomes very long, making the SEMs apparatuses of no practical use.

As an apparatus used for solving the problems described above, there is known an inspection apparatus using an electron beam for detecting a defect on a wafer by comparison of pictures. The apparatus is characterized in that: a large current electron beam is used; a specimen stage is continuously moved while the electron beam is being radiated to a specimen; a high acceleration voltage is used to accelerate the electron beam generated by an electron source; a retarding voltage is applied to the specimen to reduce the speed of the electron beam so as to prevent the specimen from being electrically-charged; and charged particles emanating from the specimen due to the radiation of the electron beam are detected after passing through an objective lens in a so-called TTL (through the lens) system.

As a result, the apparatus described above allows a mask or a pattern on a wafer serving as a specimen to be inspected for a defect with a higher degree of efficiency than the conventional SEM. It should be noted that this related technology is disclosed in documents such as Japanese Patent Laid-open No. Hei 5-258703.

With the TTL system whereby charged particles emanating from a specimen are detected after passing through an objective lens, the distance from the specimen to the objective lens can be shortened. As a result, the objective lens can be used at a short focal distance, allowing the amount of aberration of the electron beam to be reduced and, hence, a high-resolution picture to be obtained. On the other hand, the TTL system brings about unnegligible problems such as a hindrance to the improvement of the scanning speed and a big rotation change of the electron beam accompanying a variation in specimen height, causing a resulting picture to rotate as well.

FIG. 13 is a diagram showing a relation between the retarding voltage and the efficiency of detection of secondary electrons. Curve (2) shows a relation for the TTL system. As shown by curve (2), the TTL system has a problem that, as the retarding voltage is reduced, the efficiency of detection of secondary electrons also decreases to such a small value that the problem caused by a low detection efficiency can not be ignored anymore. Secondary electrons emanating from a specimen converge after passing through a magnetic field of an objective lens. The position of convergence in the axial direction changes when the retarding voltage is modified due to a variation in electron beam radiation energy. This phenomenon is the main reason why the efficiency of detection of secondary electrons decreases.

SUMMARY OF THE INVENTION

It is thus a first object of the present invention to provide an inspection method capable of increasing the speed of scanning a specimen using an electron beam and an inspection system adopting the method.

It is a second object of the present invention to provide an inspection method using an electron beam resulting in a small picture rotation and an inspection system adopting the method.

It is a third object of the present invention to provide an inspection method using an electron beam resulting in a small change in efficiency of detection of charged particles and an inspection system adopting the method.

In a configuration of the present invention, an electron beam generated by an electron source is converged on a specimen by means of an objective lens; the specimen is scanned by using the electron beam; and charged particles emanating from the specimen due to the scanning operation are detected by means of a charged particle detector provided between the specimen and the objective lens.

In another configuration of the present invention, an electron beam generated by an electron source is converged so as to generate a crossover and the electron beam is converged on a specimen by means of an objective lens provided between the crossover and the specimen; the specimen is scanned by using the electron beam; and charged particles emanating from the specimen due to the scanning operation are detected by means of a charged particle detector provided between the specimen and the objective lens.

In still another configuration of the present invention, an electron beam generated by an electron source is converged so as to generate a crossover while the electron beam is being converged on a specimen by means of an objective lens provided between the crossover and the specimen; the specimen is scanned by using the electron beam while the specimen is being moved continuously; and charged particles emanating from the specimen due to the scanning operation are detected by means of a charged particle detector provided between the specimen and the objective lens.

Then, charged particles detected by the charged particle detector are converted into an electrical signal conveying picture information and pictures are compared with each other on the basis of the picture information in order to detect a defect.

The comparison of pictures to detect a defect as described above includes comparison of a picture of an area on a specimen with a picture of another area on the same specimen and comparison of a picture of a an area on a specimen with a reference picture provided in advance.

According to a preferred embodiment of the present invention, a voltage for decelerating an electron beam is applied to a specimen. The voltage works as an acceleration voltage for charged particles emanating from the specimen, causing the charged particles to tend to form parallel beams.

According to another preferred embodiment of the present invention, charged particles emanating from the specimen are deflected by a deflection electric field and a deflection magnetic field which are substantially orthogonal to each other in the same direction. The amount of deflection of an electron beam radiated to a specimen by the deflection electric field and the amount of deflection of the electron beam by the deflection magnetic field are substantially equal to each other in magnitude but have mutually opposite directions so that one of the deflections cancels the other. As a result, a disturbance to deflection of an electron beam, that is radiated to the specimen, caused by the deflection electric field and the deflection magnetic field does not substantially exist.

According to still another preferred embodiment of the present invention, since charged particles are detected without passing through an objective lens, unlike the TTL system, even if a retarding voltage is reduced, the efficiency of detection of secondary electrons does not decrease and, in addition, the rotation of a picture can be made small.

According to a further preferred embodiment of the present invention, secondary electrons of charged particles emanating from a specimen are radiated to a conductive secondary-electron generating substance for further generating secondary electrons to be detected by a charged particle detector.

According to a still further preferred embodiment of the present invention, an electron beam is put in a blanked state with a crossover of the electron beam serving as a fulcrum. If the electron beam is parallel beams with no crossover, the position of radiation of the blanked electron beam on a specimen changes, giving rise to a problem that an area adjacent to a radiation area is electrically charged inadvertently. In the case of this embodiment, however, since the electron beam is put in a blanked state with a crossover thereof serving as a fulcrum, the position of radiation of the electron beam on the specimen does not change, allowing the problem to be solved.

BRIEF DESCRIPTION OF THE DRAWINGS

An embodiment of the present invention will be described by referring to the following diagrams wherein:

FIG. 4 is a flowchart showing a procedure for inspecting a circuit pattern created on a semiconductor wafer;

DETAILED DESCRIPTION OF THE PREFERRED EMBODIMENT

The present invention will become more apparent from a careful study of the following detailed description of a preferred embodiment with reference to the accompanying diagrams.

Figure 2:
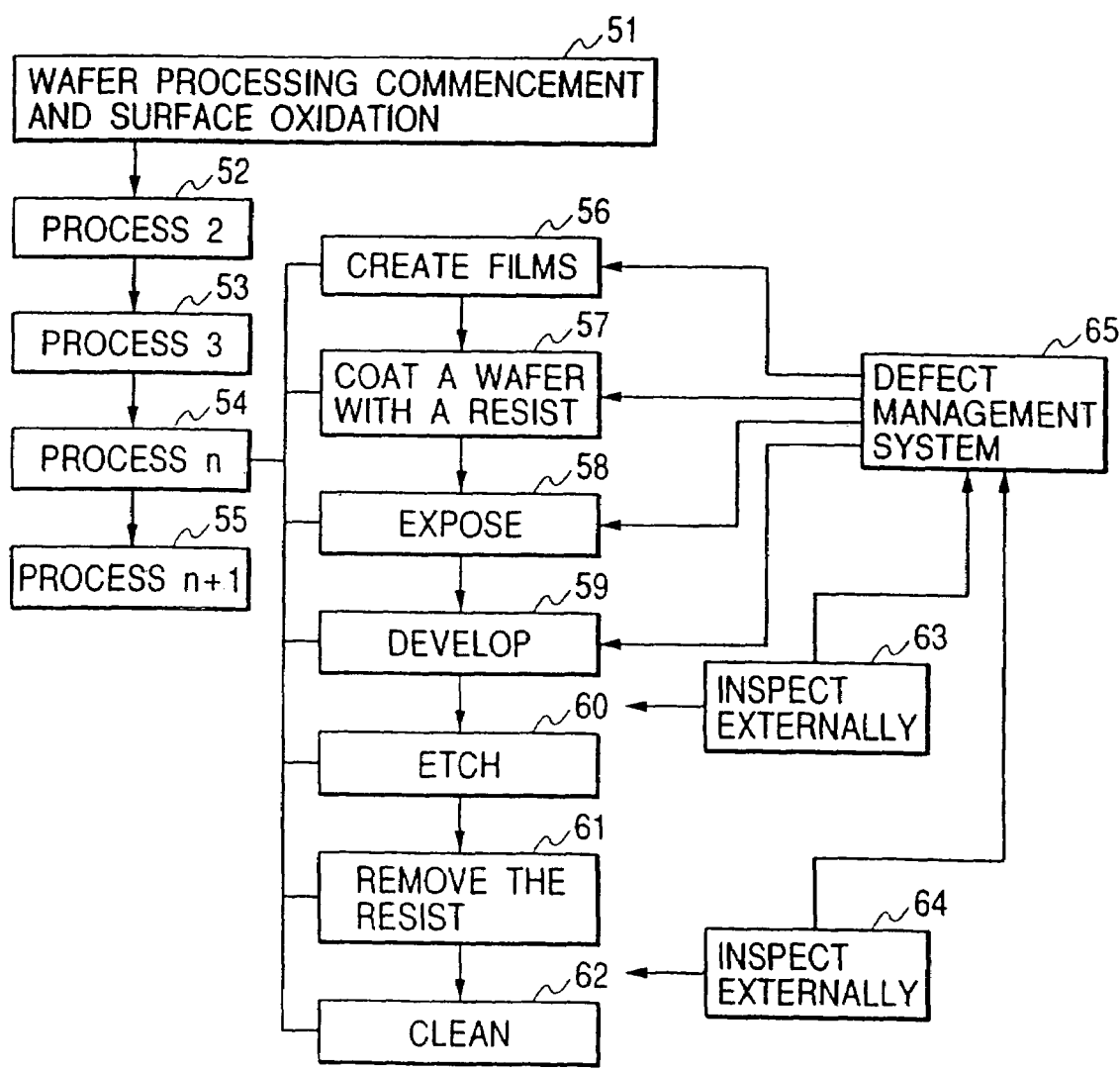
FIG. 2 is a block diagram showing a flow of a general process of fabricating a semiconductor device.

FIG. 2 is a block diagram showing a flow of a general process of fabricating a semiconductor device. As is obvious from the figure, in a process of fabricating semiconductor devices, steps 51 to 55 are repeated to create a number of patterns of semiconductor devices on wafers. Each of the steps to create a pattern comprises roughly a film creation step 56, a resist coating step 57, an exposure step 58, a development step 59, an etching step 60, a resist removing step 61 and a cleaning step 62. A circuit pattern will not be created normally on the wafer unless fabrication conditions are optimized at each of the steps.

External inspection steps 63 and 64 to inspect a circuit pattern are provided between the steps described above. When a defect is detected as a result of the inspections carried out at the steps 63 and 64, the result of the inspections is reflected in a step in the process which has generated the defect so that generation of similar defects can be suppressed. The result of the inspection is reflected typically by letting a defect control system 65 shown in FIG. 2 transmit data to pieces of fabrication equipment of the steps 56, 57, 58 and 59 of the process where fabrication conditions are changed automatically in accordance with the data.

Figure 3A:
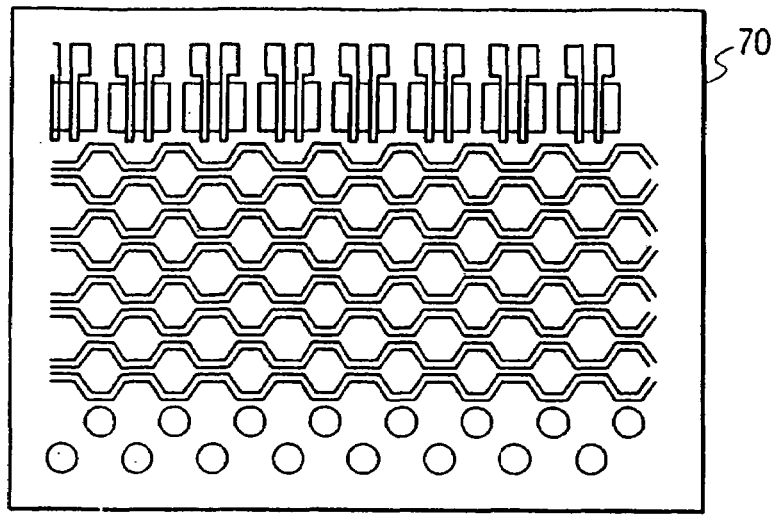
FIGS. 3(a) and 3(b) are diagrams each showing an example of a picture obtained as a result of observation of a circuit pattern on a semiconductor wafer by means of an SEM in a process of fabrication of a semiconductor device.
Figure 3B:
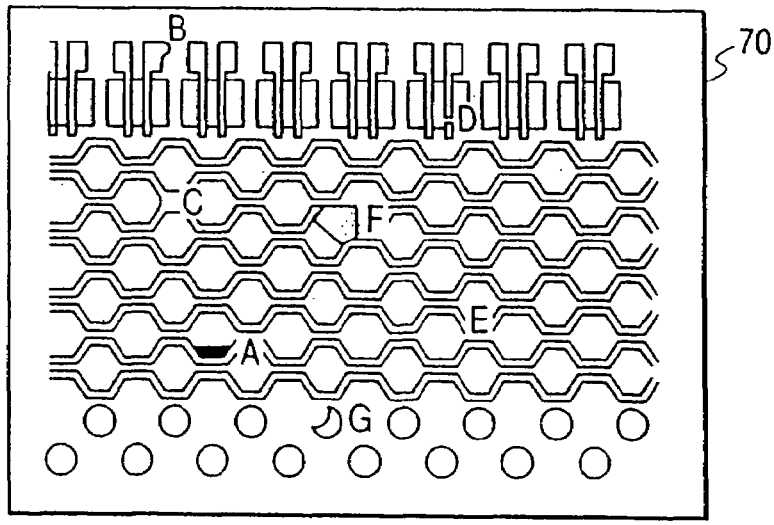

FIGS. 3(a) and 3(b) are diagrams each showing an example of a picture 70 obtained as a result of observation of a circuit pattern on a semiconductor wafer by means of a scanning electron microscope (SEM) in a process of fabrication of a semiconductor device. To be more specific, FIG. 3(a) is a diagram showing a circuit pattern obtained as a normal result of a fabrication process and FIG. 3(b) is a diagram showing a circuit pattern with a fabrication defect. For example, when an abnormality is resulted in at the film creation step 56 shown in FIG. 2, particles are stuck to the surface of a semiconductor wafer, becoming an isolated defect A on the picture shown in FIG. 3(b). In addition, when fabrication conditions such as the focus and the exposure time at the exposure step 58 following the resist coating step 57 are not optimum, there will be generated spots at which the intensity and quantity of light radiated to the resist are either excessive or insufficient, resulting in a short C, a disconnection E, a thinning or an omission D on the picture shown in FIG. 3(b). If a defect results on a reticle or a mask at the exposure step 58, a shape abnormality of the pattern will be prone to generation.

In addition, if the amount of etching is not optimized or if a thin film or particles are generated at the etching step 60, a bad aperture G is also generated besides the short C, a protrusion B and the isolated defect A. At the cleaning step 62, abnormal oxidation is apt to occur at places like a pattern corner due to draining conditions during a drying process, resulting in a thin film residual F which is difficult to observe by means of an optical microscope.

Thus, in a wafer fabrication process, it is necessary to optimize fabrication conditions so that these kinds of defect are not generated and to early detect a generated abnormality and to feed back information on the defect to a step at which the abnormality has been generated.

As described above, in order to detect a defect like the one described above, external inspections 63 and 64 are typically carried out after the development step 59 and the resist removing step 61 respectively as shown in FIG. 2. In these external inspections, an inspection apparatus of the present invention using an electron beam is used.

Figure 1:
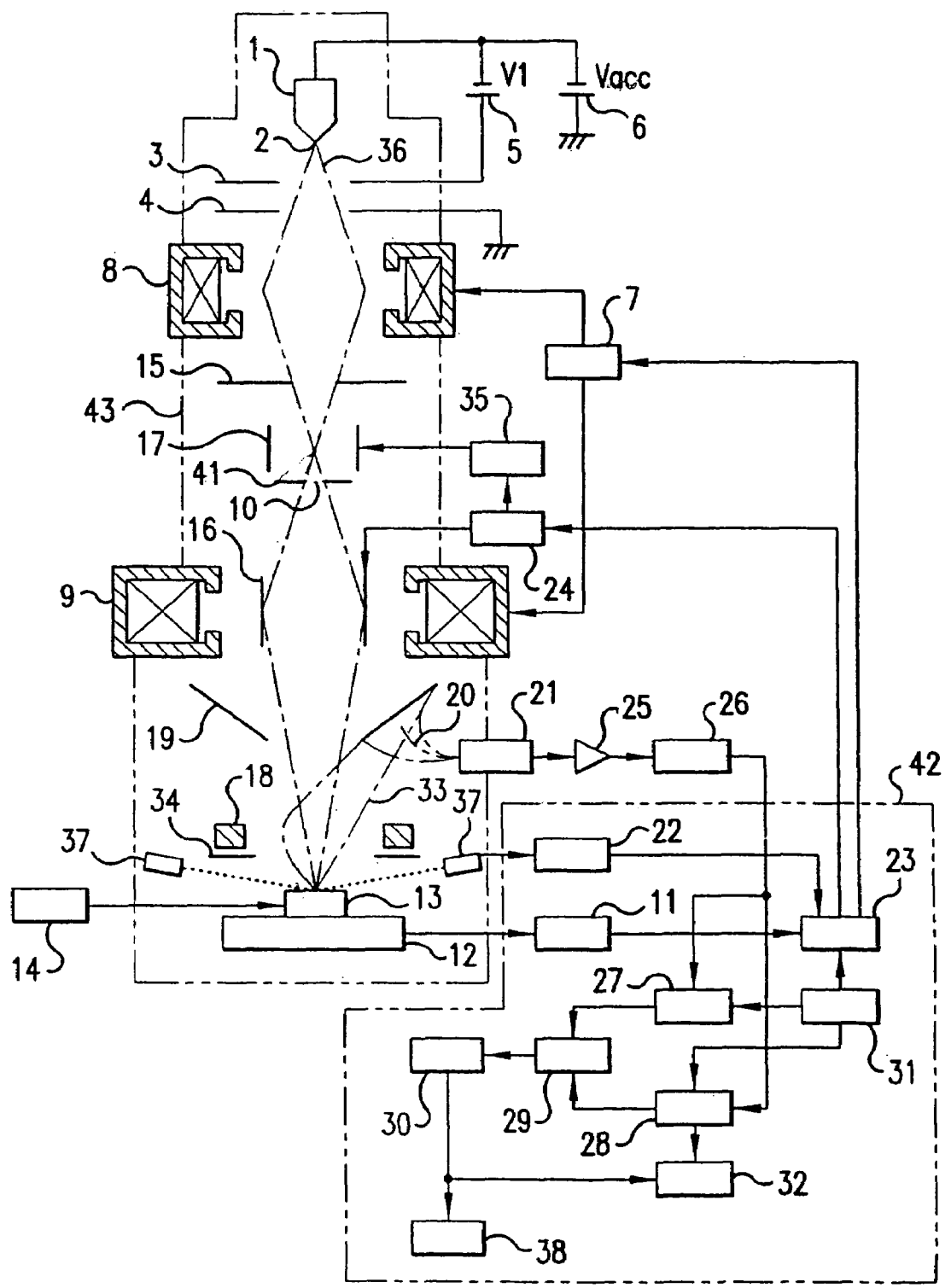
FIG. 1 is a longitudinal sectional view showing the configuration of an inspection system using an electron beam as implemented by an embodiment of the present invention in a simple and plain manner.

FIG. 1 is a longitudinal sectional view showing the configuration of an inspection system using an electron beam as implemented by the embodiment of the present invention in a simple and plain manner.

In the inspection system shown in FIG. 1, an electron gun 1 comprises an electron source 2, a drawing electrode 3 and an acceleration electrode 4. A drawing voltage V1 is generated between the electron source 2 and the drawing electrode 3 by a drawing power supply 5 to draw an electron beam 36 from the electron source 2. The acceleration electrode 4 is sustained at the earth electric potential. An acceleration voltage Vacc is generated between the acceleration electrode 4 and the electron source 2 by an acceleration power source 6 to accelerate the electron beam 36.

The accelerated electron beam 36 is converged by a first convergence lens 8 so as to generate a crossover 10 between the first convergence lens 8 and an objective lens 9 which serves as a second convergence lens. The first and second convergence lenses 8 and 9 are connected to a lens power supply 7. The electron beam 36 is further converged by the objective lens 9 on a specimen 13 such as a semiconductor wafer placed on a specimen stage 12 which can be moved horizontally by a stage driving unit not shown in the figure and a length measuring unit 11 for position monitoring use. That is to say, the converged electron beam 36 is radiated to the specimen 13. The configuration described above is accommodated in a container 43 which sustains a vacuum environment appropriate for radiation of the electron beam 36.

A negative voltage is applied to the specimen 13 as a retarding voltage for decelerating the electron beam 36 by a variable deceleration power supply 14. A voltage is further applied by an electrode 34 in the positive direction to the specimen 13. The electrode 34 is provided between the specimen 13 and the objective lens 9. Thus, the electron beam 36 is decelerated by the retarding voltage. Normally, the electrode 34 is set at the earth electric potential and the retarding voltage can be changed arbitrarily by adjusting the variable deceleration power supply 14.

A diaphragm 15 is provided between the first convergence lens 8 and the crossover 10 whereas a diaphragm 41 is provided between the crossover 10 and an electron beam scanning deflector 16. The diaphragms 15 and 41 shield excessive electrons and are also useful for determination of an angular aperture of the electron beam 36.

Provided between the crossover 10 and the objective lens 9, the electron beam scanning deflector 16 has a function to deflect the converged electron beam 36 so as to let the electron beam 36 scan the specimen 13. The electron beam scanning deflector 16 is provided inside the objective lens 9 at such a position that a fulcrum of the deflection thereof substantially coincides with the center of a magnetic pole gap of the objective lens 9. As a result, the amount of deflection distortion can be reduced.

Provided between the diaphragm 15 and the electron beam scanning deflector 16, a blanking deflector 17 is used for deflecting and blanking the electron beam 36 at a position where the crossover 10 is created. The blanking deflector 17 is connected to a scanning-signal generating unit 24.

FIG. 4 is a flowchart showing a procedure for inspecting a circuit pattern created on a semiconductor wafer by using an inspection system provided by the present invention.

First of all, the specimen 13 is mounted on the specimen stage 12 and, then, the specimen stage 12 is moved to the inside of the container 41. Subsequently, air is exhausted from a specimen inspection chamber inside the container 41 to put the chamber in a vacuum state and a retarding voltage is applied to the specimen 13.

When the specimen 13 is scanned by using the converged electron beam 36, reflected electrons and secondary electrons 33, charged particles, emanate from the specimen 13. The secondary electrons 33 are defined as electrons each having an energy of 50 eV or smaller.

Since positive and negative directions of the secondary electrons 33 are just opposite to those of the electron beam 36 radiated to the specimen 13, the retarding voltage generated to decelerate the electron beam 36 works as an acceleration voltage for the secondary electrons 33. Thus, since the secondary electrons 33 are accelerated by the retarding voltage, the directions of the secondary electrons are uniform. As a result, the secondary electrons 33 form substantially parallel beams entering an E×B (E Cross B) deflector 18 which is provided between the specimen 13 and the objective lens 9.

Provided with a deflection electric-field generator for generating a deflection electric field for deflecting the secondary electrons 33, the E×B deflector 18 also includes a deflection magnetic-field generator for generating a deflection magnetic field for canceling the deflection of the electron beam 36 radiated to the specimen 13 by the deflection electric field. The deflection magnetic field is generated in a direction perpendicular to the direction of the deflection electric field. Therefore, the deflection electric field works to deflect the secondary electrons 33 in almost the same direction as the deflection magnetic field. Thus, the deflection electric field and the deflection magnetic field generated by the E×B deflector 18 deflect the accelerated secondary electrons 33 without having a bad effect on the electron beam 36 radiated to the specimen 13 because of the mutual cancellation.

In order to sustain each of the deflection angles at a substantially fixed value, the deflection electric field and the deflection magnetic field generated by the E×B deflector 18 can be changed in a way interlocked with a variation in retarding voltage. Used for generating a deflection electric field and a deflection magnetic field, the E×B deflector 18 is also referred to as a deflection electric-field/deflection magnetic-field generator in some cases.

The secondary electrons 33 deflected by the deflection electric field and the deflection magnetic field generated by the E×B deflector 18 are radiated to a secondary-electron generating substance 19, colliding with the secondary-electron generating substance 19. The secondary-electron generating substance 19 is provided between the objective lens 9 and the E×B deflector 18 around the axis of the electron beam 36. The secondary-electron generating substance 19 has a shape resembling a cone with the lateral cross-sectional area thereof increasing along the axis in the direction toward the electron gun 1. The secondary-electron generating substance 19 is made of CuBeO and has a capability of generating second secondary electrons 20 five times the hitting secondary electrons in number. The second secondary electrons 20 emanating from the secondary-electron generating substance 19 which each have an energy of 50 eV or smaller are detected by a charged particle detector 21, being converted into an electrical signal.

The height of the specimen 13 is measured by an optical specimen-height measurement unit 22 in a real-time manner and the measured height is fed back to the lens power supply 7 through a correction control circuit 23 for correcting the focal distance of the objective lens 9 dynamically. In addition, the position of radiation of the electron beam 36 on the specimen 13 is detected by a length measurement unit 11 for position monitoring and the detected radiation position is fed back to a scanning-signal generation unit 24 through the correction control circuit 23 for controlling the position of radiation of the electron beam 36 on the specimen 13.

Figure 5:
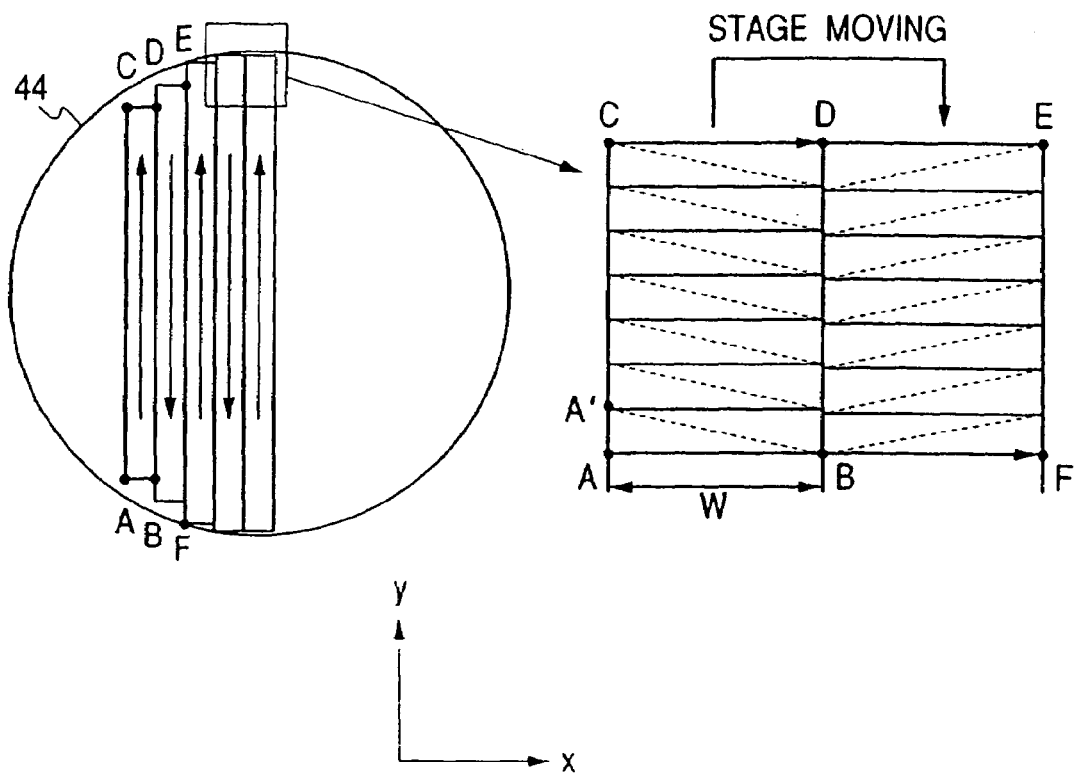
FIG. 5 is a diagram showing a plan view of a wafer seen from a position above the wafer.
Figure 6:
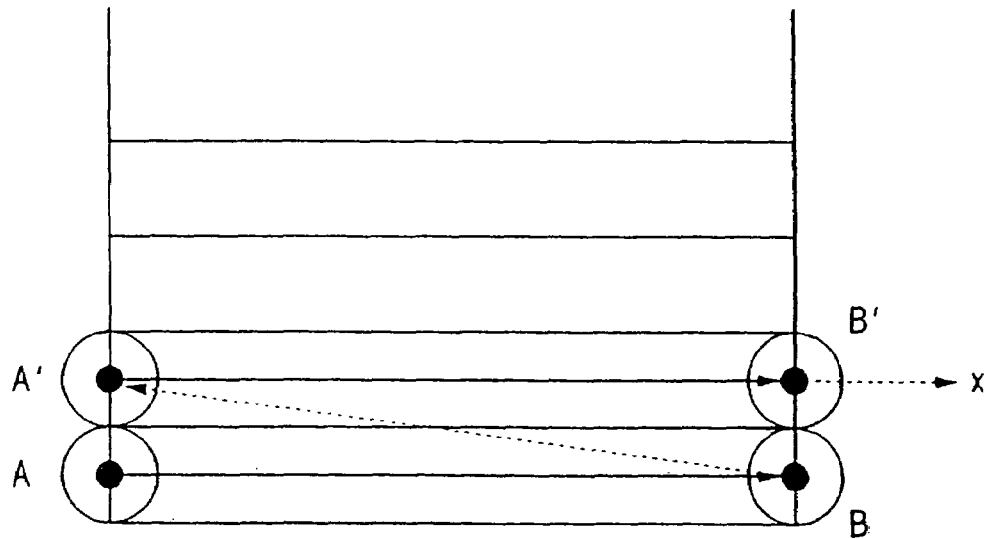
FIG. 6 is an enlarged diagram showing a portion of the wafer shown in FIG. 5.

FIG. 5 is a diagram showing a plan view of a semiconductor wafer 44, an example of the specimen 13, as seen from a position above the wafer 44 and FIG. 6 is an enlarged diagram showing a portion of the wafer 44 shown in FIG. 5. The wafer 44 is continuously moved by a stage driving unit not shown in the figure in the y direction of x-y coordinates as indicated by an arrow y. On the other hand, an operation to scan the wafer 44 by using the electron beam 36 is carried out in the x direction indicated by an arrow x. The scanning operation comprises actual scanning sweeps and a blanked-state sweeps in the x direction which are repeated alternately.

In order to radiate the electron beam 36 to correct positions on the wafer 44 with correct timing, during a fly-back period of the scanning operation, that is, during a blanked-state sweep, the electron beam 36 is deflected and blanked by means of the blanking deflector 17 shown in FIG. 1 so that the electron beam 36 is not directed toward the wafer 44.

An operation to scan the wafer 44 by using the electron beam 36 is started at a point A shown in FIG. 5 and carried out till a point B. While the scanning operation is being carried out, the wafer 44 is moved along with the specimen stage 12 in the y direction. Then, between the point B and a point A', the electron beam 36 is put in a blanked state as shown by a dashed line prior to resumption of the scanning from the point A' to a point B'. For more information refer to FIG. 6. While repeating the actual scanning and blanked-state sweeps alternately in this way, a scanning operation is continued to a line between points C and D.

After the scanning operation from the point A to the point C on the wafer 44 has been completed, the wafer 44 is moved to the left in the x direction by a distance equal to the scanning width w, shifting the position of radiation from the point C to a point D. Then, the scanning operation by using the electron beam 36 from the point A to the point C is repeated now from the point D to the point B by repeating the actual scanning and blanked-state sweeps alternately while the wafer 44 is being moved this time in the y direction. After the scanning operation from the point D to the point B on the wafer 44 has been completed, the wafer 44 is moved to the left in the x direction by a distance equal to the scanning width w, shifting the position of radiation from the point B to a point F.

By repeating the scanning operations from the point A to the point F described above, the entire surface of the wafer 44 is scanned by using the electron beam 36.

Figure 7A:
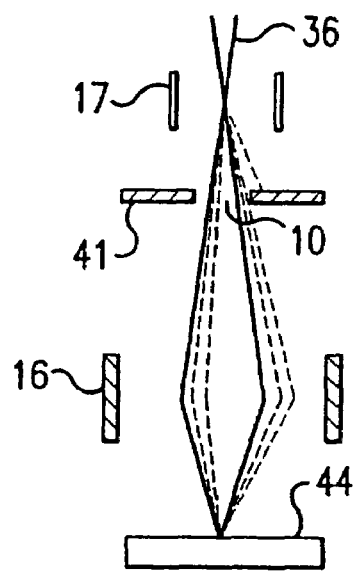
FIGS. 7(a) and 7(b) are conceptual diagrams showing a blanked state of an electron beam.
Figure 7B:
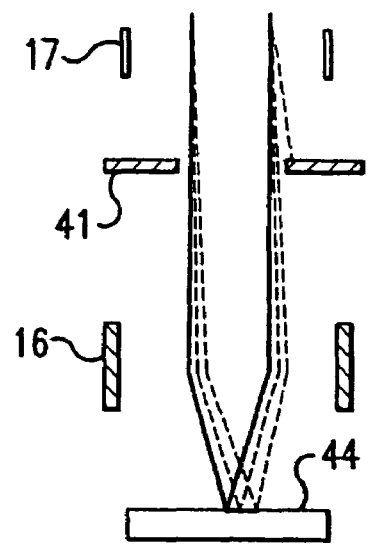

FIGS. 7(a) and 7(b) are conceptual diagrams showing a blanked state of the electron beam 36 shown in FIG. 1.

In the present embodiment, the electron beam 36 shown in FIG. 1 is put in a blanked state with the crossover 10 of the electron beam 36 taken as a fulcrum as shown in FIG. 7(a). If the electron beam 36 is deflected with a point other than the crossover 10 taken as a fulcrum in order to put the electron beam 36 in a blanked state, the position of radiation of the electron beam 36 on the wafer 44 is inadvertently shifted during the deflection. FIG. 7(b) is a diagram showing a case in which the electron beam 36 is parallel beams. In this case, when the electron beam 36 is put in a blanked state, there results in a beam that can not be shielded by the diaphragm 41 during the blanking operation. Such a beam is inadvertently radiated to a small adjacent region which is not supposed to be exposed to the beam. As a result, during the blanking operation, an area naturally not supposed to experience radiation by the electron beam 36 is inadvertently exposed to the electron beam 36 to result in a wrong picture. In order to solve this problem, in the embodiment of the present invention, the electron beam 36 is deflected with the crossover 10 taken as a fulcrum during a blanking operation. As a result, the position of radiation of the electron beam 36 on the wafer 44 can be prevented from being shifted, making it possible to avoid an incorrect resulting picture.

The scanning operation of the specimen 13 or the wafer 44 by using the electron beam 36 is carried out by deflecting the electron beam 36 in the x direction while continuously moving the specimen 13 or the wafer 44 in the y direction. Instead of repeating actual scanning and blanked-state sweeps alternately as described above, consecutive actual scanning sweeps can be carried out back and forth. In this case, the sweeping speed in an onward deflection is set at a value equal to the sweeping speed in a retreat deflection. In such a scheme, the blanking deflector 17 can be eliminated and the scanning time can be shortened by periods required to blank the electron beam 36. In this case, however, care must be exercised as follows.

Figure 8:
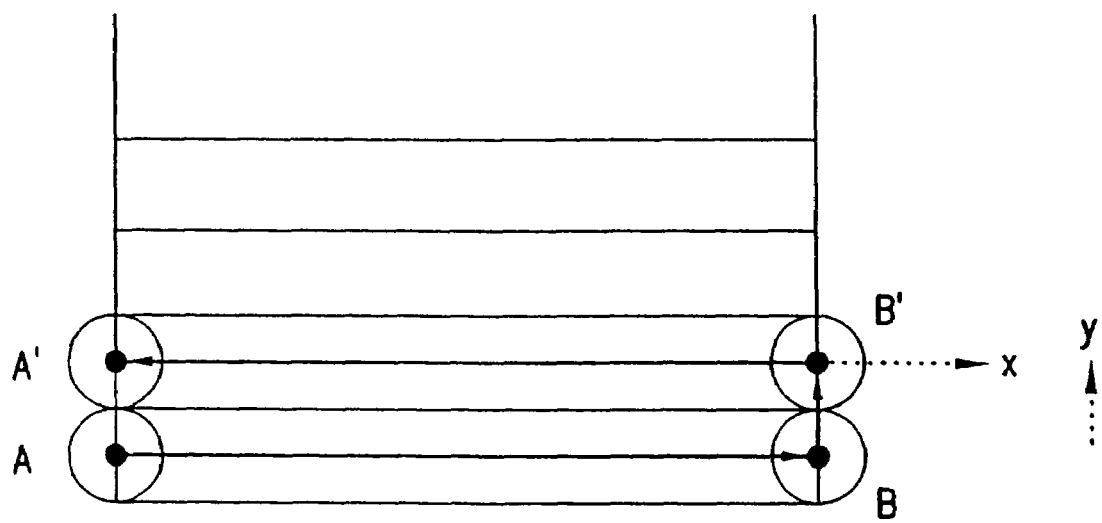
FIG. 8 is an enlarged diagram similar to FIG. 6 showing a portion of the wafer shown in FIG. 5.

FIG. 8 is an enlarged diagram similar to FIG. 6 showing scanning directions of the electron beam 36 on a portion of the wafer 44 shown in FIG. 5. The end and start points B and B' of a back-and-forth deflection of the electron beam 36 on the wafer 44 are exposed to the focused electron beam 36 radiated thereto during a short period of time. To put it in detail, at the end point B of a scanning sweep in the x direction from the left to the right, the movement of the electron beam 36 in the x direction is halted to wait for the position of radiation to be shifted to the start point B' by a movement of the wafer 44 in the y direction by a distance equal to the scanning width. After the position of radiation has been shifted to the start point B', the position of radiation is moved from the right to the left in the x direction. During the period of time to wait for the position of radiation to be shifted in the y direction to the start point B', the radiation of the electron beam 36 is continued in the y direction along a distance on the wafer 44 from an area centering at the end point B to an area centering at the start point B'. For this reason, in the case of a specimen 13 exhibiting an electrically charging phenomenon with an extremely short time constant, the brightness of a picture taken from these areas will not be uniform. In order to make the amount of radiation provided by the electron beam 36 substantially uniform over the entire surface of the wafer 44, the scanning speed of the electron beam 36 is controlled so that the speed along a line between the points B and B' is set at a value higher than the speed along a line between the points A and B shown in FIG. 8.

Next, picture processing carried out by a picture processing unit 42 shown in FIG. 1 is explained.

The picture processing unit 42 detects a defect on the specimen 13 from an electrical signal supplied by the charged particle detector 21 by way of an amplifier 25 and an A/D converter 26. To put it in detail, the picture processing unit 42 detects the number of second secondary electrons and converts the number of second secondary electrons into an electrical signal which is amplified by the amplifier 25 before being converted by the A/D converter 26 into digital data. The digital data is stored in storage units 27 and 28 employed in the picture processing unit 42 as a picture signal. To put it concretely, first of all, a picture signal representing the number of second secondary electrons corresponding to a first inspection area on the wafer 44 is stored in the storage unit 27.

Then, a picture signal representing the number of second secondary electrons corresponding to a second inspection area on the wafer 44 adjacent to the first inspection area with the same circuit pattern is stored in the storage unit 28 while, at the same time, the picture signal for the second inspection area is being compared with the picture signal for the first inspection area. Subsequently, a picture signal representing the number of second secondary electrons corresponding to a third inspection area on the wafer 44 is stored in the storage unit 27 while, at the same time, the picture signal for the third inspection area is being compared with the picture signal for the second inspection area stored in the storage unit 28. These operations are repeated to store and compare picture signals for all inspection areas on the wafer 44. It should be noted that a picture signal stored in the storage unit 28 is displayed on a monitor 32.

A picture signal is compared with another picture signal by a processing unit 29 and a defect judgment unit 30 shown in FIG. 1. The processing unit 29 computes a variety of statistics such as averages of picture concentration values, variances and differences among peripheral pixels for secondary-electron picture signals stored in the storage units 27 and 28 on the basis of defect judgment conditions already found. Picture signals completing the processing carried out by the processing unit 29 are supplied to the defect judgment unit 30 to be compared with each other to extract a difference signal. The defect judgment conditions found and stored in memory before are referred to in order to split the difference signal into a defect signal and a signal other than the defect signal.

Figure 9A:
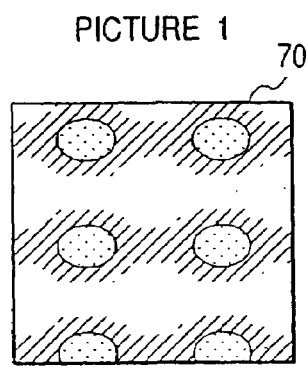
FIGS. 9(a) to 9(c) are diagrams showing pictures to be compared with each other and a result of the comparison.
Figure 9B:
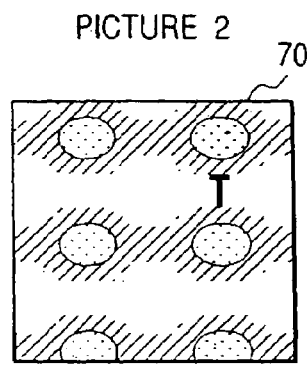
Figure 9C:
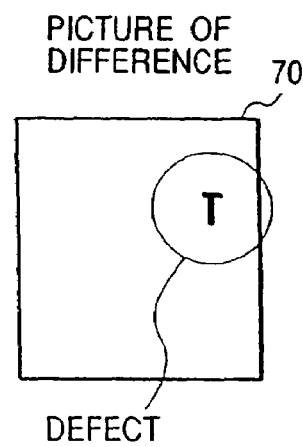

FIGS. 9(a) to 9(c) are diagrams showing pictures 70 to be compared with each other in an example of comparison and a result of the comparison. To be more specific, FIG. 9(a) shows a secondary-electron picture signal stored in the storage unit 27 and FIG. 9(b) shows a secondary-electron picture signal stored in the storage unit 28. If picture 1 shown in FIG. 9(a) is subtracted from picture 2 shown in FIG. 9(b), a difference picture representing a defect shown in FIG. 9(c) is obtained.

As an alternative, a picture signal representing the number of second secondary electrons corresponding to an inspection area of a circuit pattern used as a standard is stored in the storage unit 27 and, then, a picture signal representing the number of second secondary electrons corresponding to an inspection area of a circuit pattern on the specimen 13 is stored in the storage unit 28 while, at the same time, the picture signal for the inspection area on the specimen 13 is being compared with the picture signal for the standard circuit pattern stored in the storage unit 27. To put in detail, first of all, an inspection area and a desired inspection condition for a good semiconductor device are input from a control unit 31 and the inspection area of the good semiconductor device is then inspected under the inspection condition. Then, a secondary-electron picture signal for the desired inspection area is fetched and stored in the storage unit 27. Subsequently, the specimen 13 serving as an inspection target is inspected in the same way as the good semiconductor device and a secondary-electron picture signal for the specimen 13 is fetched and stored in the storage unit 28. At the same time, the secondary-electron picture for the specimen 13 is compared with the secondary-electron picture of the good semiconductor device stored in the storage unit 27 after the position of the former is adjusted to the latter to detect a defect.

As the good semiconductor device used in the above alternative method, a good portion of the specimen 13, or a good wafer or a good chip other than the specimen 13 can be used. In the specimen 13, for example, a defect may be generated due to a shift generated in adjustment of a lower-layer pattern and an upper-layer pattern in creation of a circuit pattern. If a circuit pattern is compared with another circuit pattern on the same wafer or the same chip, defects generated uniformly over the entire wafer like the defect described above are overlooked. If the picture signal for the specimen 13 is compared with a picture signal for a good device stored in advance, on the other hand, the defects generated uniformly over the entire wafer can also be detected.

The control unit 31 shown in FIG. 1 issues an operation instruction to components of the inspection system and sets conditions for the components. Thus, a variety of conditions including information on an acceleration voltage, a deflection width (or a scanning width) and a deflection speed (or a scanning speed) of the electron beam, a movement speed of the specimen stage and timing to fetch a signal output by the detector are supplied to the control unit 31 in advance.

The following is a description of differences between the inspection system using an electron beam according to the present invention and the conventional scanning electron microscope referred to hereafter simply as an SEM. In the following description, the inspection system using an electron beam according to the present invention is referred to hereafter simply as the present inspection system for the sake of convenience.

An SEM is an apparatus used for observing a very limited area, for example, an area of several tens of square µm at a high magnification over a relatively long period of observation time. Even with a length measurement scanning electron microscope referred to hereafter simply as a length measurement SEM, one of semiconductor inspection apparatuses, the user is capable of doing no more than observation and measurement of only a limited plurality of points on a wafer. On the other hand, the present inspection apparatus is equipment for searching a specimen such as a wafer for a location on the specimen at which a defect exists. Thus, since the present inspection apparatus has to inspect an extremely large area in every nook and corner, the fact that the inspection must be carried out at a high speed is an important requirement.

Figure 10:
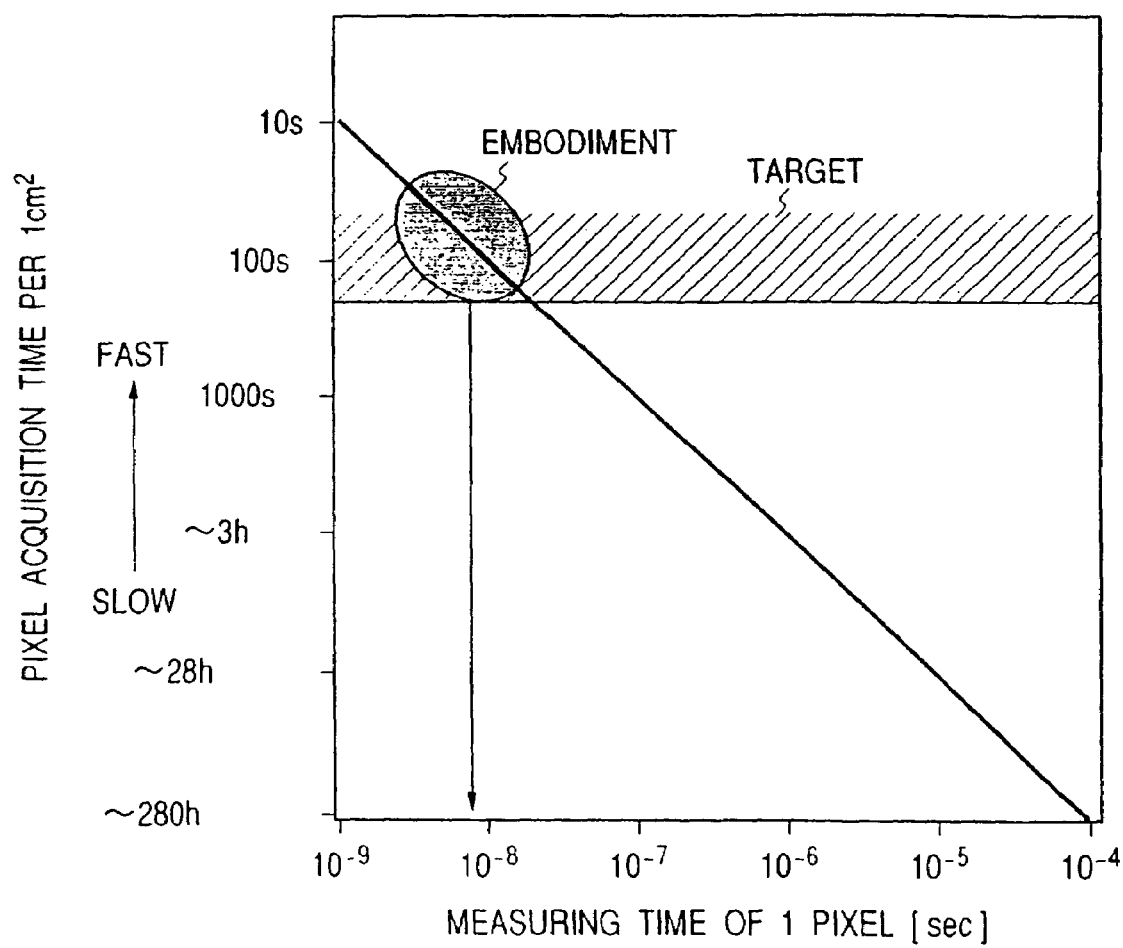
FIG. 10 is a diagram showing a relation between the picture acquisition time per $cm^2$ and the measurement time per pixel.
Figure 11:
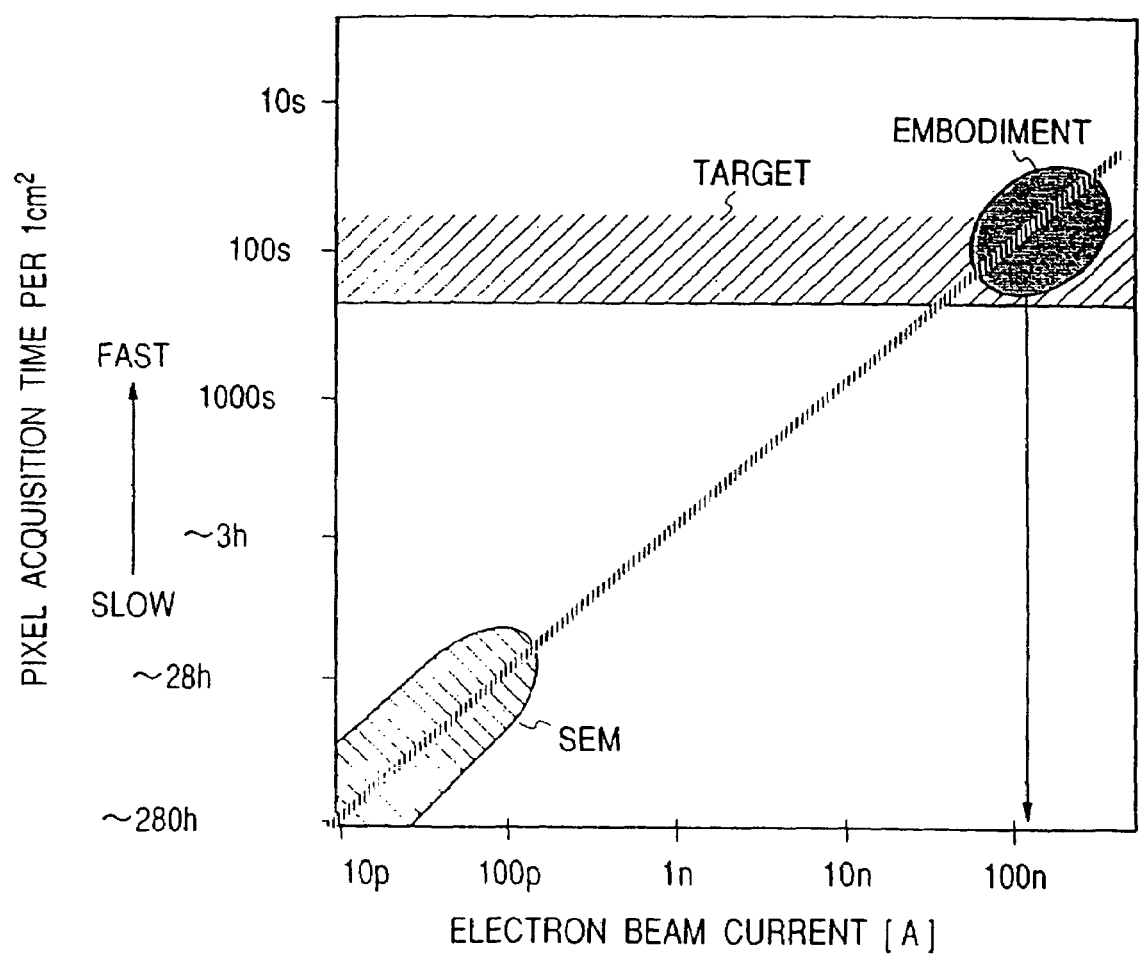
FIG. 11 is a diagram showing a relation between the picture acquisition time per $cm^2$ and the current of an electron beam.

FIG. 10 is a diagram showing a relation between the picture acquisition time per $cm^2$ and the measurement time per pixel and FIG. 11 is a diagram showing a relation between the picture acquisition time per $cm^2$ and the current of an electron beam.

In general, an S/N ratio of an electron beam picture has a correlation with the square root of the number of radiated electrons per pixel in an electron beam radiated to a specimen. A defect to be detected from a specimen is such an infinitesimal defect that inspection by pixel comparison is desirable. From the size of a pattern to be inspected, assume that the demanded resolution of the inspection system is set at a value of the order of 0.1 µm. In this case, the pixel size is also about 0.1 µm. From this point of view and experiences gained by the inventors, it is desirable to have a raw picture prior to picture processing with an S/N ratio of at least 10 after detection by a charged particle detector. On the other hand, the length of an inspection time required in inspection of circuit patterns on a wafer is generally about 200 $sec/cm^2$. If the length of a time required only for acquisition of a picture is about half the inspection time which is about 100 $sec/cm^2$, the measurement time of 1 pixel is equal to or smaller than 10 nsec as shown in FIG. 10. In this case, since the number of electrons required per pixel is 6,000, it is necessary to set the electron beam current at at least 100 nA as shown in FIG. 11. In the case of an SEM or a length measurement SEM, even a slow picture acquisition time per pixel does not give rise to a problem in the practical use. Thus, an electron beam current of several hundreds of pA or smaller can be used as shown in FIG. 11.

Taking the things described above into consideration, in the embodiment of the present invention, the current of an electron beam radiated to a specimen, the pixel size, the spot size of the electron beam on the specimen and the continuous movement speed of the specimen stage 12 are set at 100 nA, 0.1 µm, 0.08 µm (a value smaller than the resolution of 0.1 µm) and 10 mm/sec respectively. Under these conditions, a high-speed inspection of 200 $sec/cm^2$ can be achieved by carrying out a scanning operation by using an electron beam on the same area of the specimen 13 only once instead of carrying out the scanning operation a plurality of times.

In the case of the conventional SEM or the conventional length measurement SEM, the current of an electron beam radiated to a specimen is in the range several pA to several hundreds of pA. Thus, the inspection time per 1 $cm^2$ would be several hundreds of hours. For this reason, the SEM or the length measurement SEM can not substantially be put to practical use for inspection of the entire surface of a specimen such as a wafer in a fabrication process.

In addition, in the embodiment with the above specifications, in order to generate a large current of the electron beam and to allow inspection to be carried out at a high speed, as the electron source 2 of the electron gun 1, a thermal electric-field emission electron source of a diffusion supply type, that is, an electron source made of Zr/O/W as a source material, is employed. Furthermore, a measurement time of 10 nsec per pixel corresponds to a 100 MHz sampling frequency of the picture. It is thus necessary to provide a charged particle detector 21 with a high response speed commensurate with the sampling frequency of 100 MHz. As a charged particle detector 21 satisfying this requirement, a PIN type semiconductor detector is employed.

In the case of a specimen exhibiting a characteristic of low conductivity or no conductivity, the specimen is electrically charged by an electron beam radiated thereto. Since the amount of electrical charge depends on the acceleration voltage of the electron beam, this problem can be solved by reducing the energy of the electrons in the beam. In an electron-beam inspection system based on picture comparison, however, a large current electron beam of 100 nA is used. Thus, if the acceleration voltage is reduced, the amount of aberration caused by a space charge effect, that is, the amount of spreading of the electron beam in the radial direction, increases so that it is difficult to obtain a 0.08-µm spot size of the electron beam on the specimen. As a result, the resolution is deteriorated.

Figure 12:
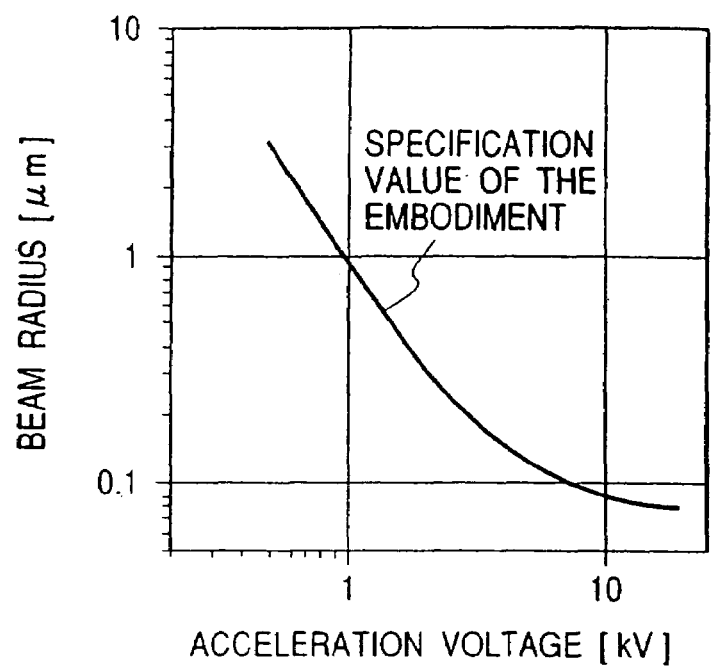
FIG. 12 is a diagram showing a relation between the diameter of an electron beam and the acceleration voltage.

FIG. 12 is a diagram showing a relation between the diameter of an electron beam and the acceleration voltage at an electron beam current of 100 nA and a specimen radiation energy of 0.5 keV. In the embodiment of the present invention, in order to prevent the resolution from deteriorating and changing due to the space charge effect and to obtain a stable 0.08-µm spot size of the electron beam on the specimen, the acceleration voltage is set at a fixed value of 10 kV as shown in FIG. 12.

The quality of a picture produced by the present inspection system is much affected by the energy of the electron beam radiated to the specimen. This energy is adjusted in accordance with the type of the specimen. When inspecting a specimen which is hardly charged electrically or when putting emphasis on the contrast of a picture in order to know an edge portion of a circuit pattern on a specimen, the amount of energy is increased. In the case of a specimen apt to be charged electrically, on the other hand, the amount of energy is decreased. It is thus necessary to find out and set an optimum radiation energy of the electron beam each time the type of a specimen to be inspected changes.

In the embodiment of the present invention, an optimum radiation energy of the electron beam radiated to a specimen 13 is set by adjusting a negative voltage applied to the specimen 13, that is, the retarding voltage, instead of changing the acceleration voltage Vacc. The retarding voltage can be changed by adjusting the variable deceleration power supply 14.

Figure 13:
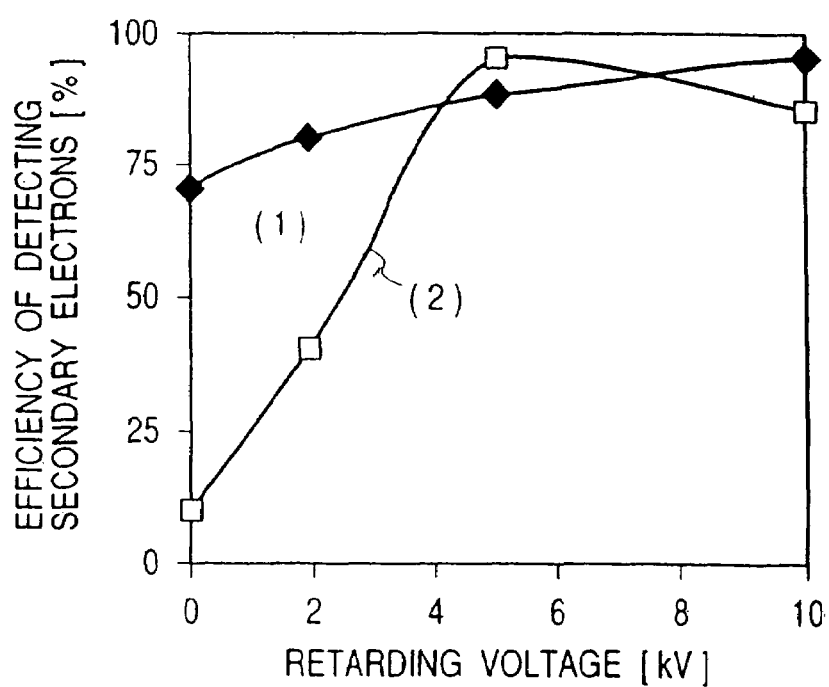
FIG. 13 is a diagram showing relations between the efficiency of detection of secondary electrons and the retarding voltage.

FIG. 13 is a diagram showing relations between the efficiency of detection of secondary electrons expressed in terms of % and the retarding voltage expressed in terms of kV. To be more specific, curve (1) shown in the figure represents a relation for a long focal distance system adopted by the embodiment of the present invention whereas curve (2) represents a relation for the TTL system adopted by the conventional inspection system. As described before, the retarding voltage should be changed in dependence on the type of the specimen and the retarding voltage exhibits an effect to accelerate secondary electrons. In the case of the TTL system, the efficiency of detection of secondary electrons varies considerably when the retarding voltage is changed as shown in FIG. 12. In the case of the embodiment of the present invention, on the other hand, the efficiency of detection of secondary electrons does not vary considerably even if the retarding voltage is changed. This is because, in the case of the TTL system, secondary electrons emanating from a specimen pass through a magnetic field of the objective lens to be converged thereby and the position of convergence in the axial direction changes with a variation in retarding voltage. The displacement of the position of convergence is the main cause of the big change in secondary-electron detection efficiency. In the case of the embodiment of the present invention, on the other hand, since secondary electrons 33 do not pass through the magnetic field of the objective lens 9, a change in retarding voltage does not have a big effect on the efficiency of detection of secondary electrons 33. In this embodiment, since the rotation of a picture is small and variations in secondary-electron detection efficiency are also small, stabilization of an inspected picture is brought about as a result.

As described before, secondary electrons 33 emanating from a specimen 13 will spread if they are left as they are. Since a retarding voltage accelerates the secondary electrons 33, putting them into substantially parallel beams, however, the efficiency of convergence of the secondary electrons 33 is improved. The secondary electrons 33 are then deflected by means of a defection electric field and a deflection magnetic field generated by the E×B deflector 18 by an angle of typically 5 degrees with respect to the center axis of the electron beam 36, hitting the secondary-electron generating substance 19. The collision of the secondary electrons 33 with the secondary-electron generating substance 19 further generates a large number of second secondary electrons 20. As a result, the efficiency of detection of secondary electrons is improved considerably by virtue of the parallel beams and the collision of the secondary electrons 33 with the secondary-electron generating substance 19

In an apparatus such as the conventional SEM, charged particles emanating from a specimen 13 are detected after passing through the objective lens 9. As described above, this system is referred to as a TTL (through the lens) system. According to the TTL system, by operating the objective lens at a short focal distance, the amount of aberration of the electron beam can be reduced, hence, allowing the resolution to be increased. In the case of the embodiment of the present invention, on the other hand, charged particles 33 emanating from a specimen 13 are detected by the objective lens 9 as shown In FIG. 1. For this reason, the focal distance of the objective lens 9 is set at a large value in comparison with the TTL system. To be more specific, in the case of the conventional TTL system, the focal distance of the objective lens is set at a value of the order of 5 mm. In the case of the embodiment of the present invention, on the other hand, the focal distance is set at a value of about 40 mm. In addition, in order to reduce the amount of aberration of the electron beam, a high acceleration voltage of 10 kV is used as described earlier.

As a result, according to the embodiment of the present invention, the deflection width of the electron beam 36 radiated for acquisition of a picture of a specimen 13, that is the width of scanning by using the electron beam 36, can be set at a large value. In the case of the conventional TTL, for example, the deflection width of the electron beam is set at a value of the order of 100 µm. In the case of the embodiment of the present invention, on the other hand, the deflection width can be set at a value of about 500 µm.

Since the surface of a specimen 13 is not a perfectly plane surface, the height of the specimen 13 changes when the position of radiation an area on the specimen 13 to be inspected is moved. It is thus necessary to operate the objective lens 9 by always adjusting the focal distance to the surface of the specimen 13 through variation of excitation of the objective lens 9. In the conventional TTL system, the objective lens is operated at a short focal distance by strong excitation. With a strongly excited objective lens, however, the flow of the electron beam exhibits a rotation in the horizontal direction accompanying a change in specimen height. As a result, since the resulting picture also rotates, it is necessary to compensate the picture for the rotation. In the case of the embodiment of the present invention, on the other hand, the objective lens 9 is operated at a long focal distance by weak excitation. Typically, the objective lens 9 is excited at IN/ (E)=9 where the symbol I is the current of the objective lens expressed in terms of amperes, the symbol N is the number of turns of a coil employed in the objective lens 9 and the symbol E is the energy of the electron beam expressed in terms of eV. As a result, even if the focal distance is adjusted little to accompany a change in height of the specimen 13, the rotation of the electron beam 36 and, hence, the rotation of the resulting picture are so small that they can be ignored, making it unnecessary to compensate the picture for the rotation.

In the embodiment of the present invention described above, secondary electrons 33 emanating from a specimen 13 are used for creating a picture. It should be noted that a picture can also be created by using electrons reflected by the specimen 13 due to radiation of the electron beam 36 thereto and scattered on the rear side of the specimen 13 to give yet the same effect.

What is claimed is:

1. An inspection method for detecting a defect of a specimen by using an electron beam, said method comprising the steps of:
    forming a crossover of the electron beam;
    determining a beam current of the electron beam based on a signal to noise ratio of an image of the defect and an inspection time;
    deflecting said electron beam set to at least 100 nA beam current by taking a crossover as a fulcrum during a flyback period of a scanning operation;
    applying a retarding voltage for decelerating the electron beam to said specimen;
    setting an electrode provided between the specimen and the crossover at a positive electric potential as compared with an electric potential of the specimen; and
    changing the magnitude of said retarding voltage based on the nature of said specimen.

2. An inspection method using an electron beam according to claim 1, further comprising the steps of:
    scanning said specimen by using said electron beam; and
    detecting charged particles emanating from said specimen and converting said detected charged particles into an electrical signal.

3. An inspection method using an electron beam according to claim 2, further comprising the steps of:
    storing picture information conveyed by said electrical signal;
    comparing a picture with another by using said stored picture information; and
    detecting a defect of said specimen.

4. An inspection method using an electron beam according to claim 3, further comprising the step of:
    continuously moving said specimen during said scanning.

5. An inspection method using an electron beam according to claim 2, wherein there are generated a deflection electric field for deflecting said charged particles in a predetermined direction and a deflection magnetic field for deflecting said charged particles in said direction as well as for canceling deflection of said electron beam by said deflection electric field.

6. An inspection method using an electron beam according to claim 2, wherein said charged particles are radiated to a secondary-electron generating substance to generate secondary electrons from said secondary-electron generating substance.

7. An inspection apparatus for detecting a defect of a specimen by using an electron beam, said apparatus comprising:

an electron source for drawing the electron beam, the beam current of the electron beam being determined based on a signal to noise ratio of an image of the defect and an inspection time;

a convergence lens for converging said electron beam so as to form a crossover between said convergence lens and said specimen;

an objective lens for converging said electron beam on the specimen;

a blanking deflector for deflecting said electron beam by taking the crossover as fulcrum during a flyback period of a scanning operation;

a scanning deflector provided inside the objective lens for deflecting said electron beam so as to let the electron beam scan the specimen;

a power supply applying a retarding voltage for decelerating the electron beam to the specimen, wherein said power supply applies a magnitude of said retarding voltage to said specimen based on the nature of said specimen; and an electrode provided between the specimen and the objective lens being set at a positive electric potential as compared with an electric potential of the specimen.

8. An inspection apparatus using an electron beam according to claim 7, further comprising:

a detector for detecting charged particles emanating from said specimen and converting said detected charged particles into an electrical signal.

9. An inspection apparatus using an electron beam according to claim 8, further comprising:

storage means for storing picture information conveyed by said electrical signal; and a comparator for comparing pictures by using said picture information.

10. An inspection apparatus using an electron beam according to claim 8, further comprising an electron beam deflector for generating a deflection electric field for deflecting said charged particles in a predetermined direction and a deflection magnetic field for deflecting said charged particles in said direction as well as for canceling deflection of said electron beam by said deflection electric field.

11. An inspection apparatus using an electron beam according to claim 8, wherein said charged particles are radiated to a secondary-electron generating substance employed therein to generate secondary electrons from said secondary-electron generating substance.

12. An inspection apparatus using an electron beam according to claim 7, wherein an electrode set at a positive electric potential with respect to said deceleration voltage is provided between said specimen and said charged particle detector.

* * * * *